United States Patent [19]

Kollar

[11] 4,393,252

[45] Jul. 12, 1983

[54] PROCESS FOR PRODUCING ETHYLENE GLYCOL

[75] Inventor: John Kollar, Wyckoff, N.J.

[73] Assignee: Redox Technologies, Inc., Wyckoff, N.J.

[21] Appl. No.: 362,433

[22] Filed: Mar. 26, 1982

Related U.S. Application Data

[63] Continuation of Ser. No. 286,721, Jul. 28, 1981, abandoned, which is a continuation-in-part of Ser. No. 183,537, Sep. 2, 1980, Pat. No. 4,337,371.

[51] Int. Cl.³ .............................................. C07C 31/20
[52] U.S. Cl. .................................... 568/852; 568/594
[58] Field of Search ........................................ 568/852

[56] References Cited

PUBLICATIONS

Oyama, "J. Org. Chem.", 30, Jul. 1965, pp. 2429–2432.

Primary Examiner—Joseph E. Evans
Attorney, Agent, or Firm—Linn I. Grim; R. M. Pritchett; M. Turken

[57] ABSTRACT

Ethylene glycol is prepared by reacting methanol and an organic peroxide of the formula $R-O-O-R_1$, wherein R and $R_1$ are each an alkyl or aralkyl group having 3 to 12 carbon atoms, in the presence of a minor amount of a basic material. Preferably, formaldehyde is present as a reactant in the presence of water. The presence of the basic material reduces the hydrogen ions which are formed and thus reduces the amount of methylal produced.

26 Claims, No Drawings

PROCESS FOR PRODUCING ETHYLENE GLYCOL

This is a continuation of application Ser. No. 286,721, filed July 28, 1981, now abandoned, which is a continuation-in-part of application Ser. No. 183,537, filed Sept. 2, 1980, now U.S. Pat. No. 4,337,371, entitled "Production of Ethylene Glycol by Reaction of Methanol, an Organic Peroxide and Formaldehyde," the disclosure which is incorporated herein by reference.

This invention relates to a process for producing ethylene glycol from methanol.

BACKGROUND OF THE INVENTION

Dwindling petroleum reserves and increasing prices have placed an increased emphasis on the use of synthesis gas in place of oil as a starting material for producing various chemicals, such as methanol, formaldehyde and ethylene glycol. The advantage of synthesis gas is that it can be produced from raw materials other than petroleum, such as natural gas or coal, and potentially from oil shale and tar sands.

An example of an industrial process for the production of ethylene glycol utilizing synthesis gas as a starting material is the reaction of formaldehyde with carbon monoxide and water at high pressures (over 300 atmospheres) in the presence of an acid catalyst to produce hydroxyacetic (glycolic) acid, which is then reacted with methanol to give the methyl ester; the latter is then converted to the glycol by catalytic hydrogenation. See U.S. Pat. Nos. 2,316,564, issued Apr. 13, 1943 to Cockerill; 2,153,064, issued Apr. 4, 1939 to Larson; and 2,152,852; 2,385,448 and 2,331,094, issued Apr. 4, 1939, June 9, 1942 and Oct. 5, 1943, respectively, to Loder.

Another proposed process utilizing synthesis gas for the production of ethylene glycol is the reaction of methanol and carbon monoxide using a rhodium-catalyzed, high pressure process; see U.S. Pat. Nos. 4,115,428, issued to Vidal et al, and 4,115,433, issued to Cosby et al on Sept. 19, 1978.

With respect to the type of process for the production of ethylene glycol disclosed and claimed herein, it should be noted that the oxidative dimerization or dehydrodimerization of a large variety of organic compounds by peroxides is very old art that was pioneered by the preeminent free radical theoretician M. S. Kharasch and his students. These studies became the foundations of much subsequent free radical chemistry. Kharasch et al in *JACS* 65, 15, 1943 show the dehydrodimerization of acetic acid to succinic acid with acetyl peroxide in a 50 mole percent utilization selectivity based on acetyl peroxide, utilization selectivity being defined as the moles of dehydrodimer product made divided by the moles of peroxide converted. Isobutyric acid produced tetramethylsuccinic acid in a 42.4 mole percent utilization selectivity. Kharasch et al in *J. Org. Chem.* 10, 386, 1945 show the ester methyl chloroacetate being dimerized to dimethyl dichlorosuccinate by acetyl peroxide in a 41 percent utilization selectivity. Kharasch et al in *J. Org. Chem.* 10, 401, 1945 show the dimerization of cumene and ethylbenzene with acetyl peroxide in 61.9 mole percent and 32.1 mole percent respectively to their dehydrodimers. Wiles et al in *I, E & C,* August 1949, page 1682, tell of the efficacy of di-t-butyl peroxide and 2,2bis-(t-butylperoxy)butane for the dimerization of cumene to 1,1,2,2-tetramethyl-1,2-diphenylethane. The benzoate ester of benzyl alcohol was dimerized to the dibenzoate ester of the corresponding glycol, 1,2-diphenylethylene glycol, with di-t-butyl peroxide by Rust et al, *JACS* 70, 3258 (1948).

The literature is replete with many other examples showing production of dehydrodimers at very low concentrations at utilization selectivities of generally from 20-50 mole percent, based on the peroxide consumed. Such selectivities are generally too low for a process to be considered for commercial development.

In connection with ethylene glycol, two teachings involving peroxide-induced reactions should be mentioned:

The first is found in Schwetlick et al, *Angew. Chem.* 72, 1960, No. 21, pages 779 and 780, and involves heating a mixture of di-tertiary-butyl peroxide and methanol in a molar ratio of 1:20 in an autoclave and/or under reflux for a period of 10 hours at 140° C. A 26 percent yield of ethylene glycol is reported, with the statement being made that an increase in the alcohol excess raises the yields.

The second and more important of such other reaction paths to ethylene glycol, in terms of its relevance to the present invention, is described by Oyama in *J. Org. Chem.* July 30, 1965, pages 2429–2432. In particular, Oyama shows the reaction of 9 moles of methanol, 1.8 moles of 15 percent aqueous formaldehyde and 0.45 moles of t-butyl peroxide (di-tertiary-butyl peroxide) at 140° C. for 12 hours to give 0.21 moles of ethylene glycol (Table I at the top of the right hand column on page 2430), with the statement being made immediately below Table I: "The yield of ethylene glycol in the reaction of formaldehyde with methanol is higher than that of t-butyl peroxide induced dimerization of methanol. This fact suggests that hydroxymethyl radical (D) adds to formaldehyde." Oyama describes in greater detail how this reaction was run and the products obtained, and contrasts it with the dehydrodimerization of methanol in the presence of t-butyl peroxide and the absence of formaldehyde, in the "Experimental" section beginning at page 2431 (particularly the sections headed "Reaction of Methanol with Formaldehyde" and "Dimerization of Methanol" on page 2432).

The yields of ethylene glycol obtained by Oyama are fairly low. Oyama's only run with methanol—that involving the above-described reaction of methanol, aqueous formaldehyde and t-butyl peroxide at 140° C. for 12 hours—gave only 1.86 weight percent of ethylene glycol.

The above-described reaction can be made to produce higher yields of ethylene glycol by substantially decreasing the amount of organic peroxide employed, relative to the amounts of formaldehyde and methanol present, from that employed by Oyama. Moreover, increasing the amount of methanol and decreasing the amount of water, relative to the other components of the reaction mixture, in contrast to the amounts employed by Oyama, also appear to contribute to the production of higher yields of ethylene glycol. Thus, for example, heating a mixture of 78.5 weight percent of methanol, 1.5 weight percent of di-tertiary-butyl peroxide, 6.9 weight percent of formaldehyde and 13.1 weight percent of water at 155° C. for 2 hours gave a yield of 4.5 weight percent of ethylene glycol in the product mixture. This is equivalent to a yield of about 7.1 moles of ethylene glycol per mole of di-tertiary-butyl peroxide employed. (Oyama obtained 0.466 mole of ethylene glycol per mole of di-tertiary-butyl peroxide in his reaction). This improvement is more fully disclosed in the copending parent of this application, U.S. Ser. No. 183,537, filed Sept. 2, 1980.

THE INVENTION

In accordance with the process of this invention, the production of a lower amount of methylal by-product in ethylene glycol produced from methanol and an organic peroxide, alone or in the presence of formaldehyde and water, is achieved by the addition to the reactants of a basic material in an amount sufficient to reduce the hydrogen ions that are being formed in the reaction without unduly reducing ethylene glycol production due to by-product formation.

It has been found that in the production of ethylene glycol from methanol and an organic peroxide, particularly in the presence of formaldehyde and water, acids such as formic acid are formed in the reaction which catalyze the formation of methylal from methanol and formaldehyde. Keeping the formation of methylal to a minimum is highly desirable in order to avoid unduly large and expensive distillation requirements necessary for the purification of the ethylene glycol product. It has been discovered that if a basic material is added to the reactants in a minor amount to reduce the hydrogen ions that are being formed from the acid production, the amounts of methylal by-product are significantly reduced. The amounts of basic material added to the reactants can be up to the amount required to neutralize or partially neutralize the acid produced to prevent it from catalyzing the reaction of methanol and formaldehyde to form methylal. If too much basic material is added to the reactants, the formaldehyde formed or added can be converted to formose sugars which will be readily apparent by the amber color and characteristic odor of the reaction liquid and the low formaldehyde accountability of the process. With too much basic material addition, very small amounts of ethylene glycol will be produced.

The term "basic material" as used in this specification and claims is meant to include those materials which will control the amount of hydrogen ions being produced in the form of acids in the reaction. Suitable basic materials include the hydroxides of alkali metals such as lithium, sodium, potassium, rubidium or cesium or alkaline earth metals such as calcium, strontium, barium, beryllium or magnesium. Also included in the term "basic material" are salts of alkali metals or alkaline earth metals and weakly ionizable acids such as oxalic, tartaric, malic, citric, formic, lactic, acetic, carbonic, phosphoric, pyrophosphoric, pyrophosphorous, propanoic, butyric, and others known in the art. Of specific interest for purposes of this invention are the sodium and potassium salts of weakly ionized acids such as acetic, formic, oxalic, carbonic (including bicarbonates) or phosphoric. Examples of these sodium and potassium salts include sodium acetate, potassium acetate, sodium bicarbonate, potassium bicarbonate, sodium formate, potassium formate, sodium oxalate, potassium oxalate, sodium carbonate, potassium carbonate, sodium pyrophosphate, potassium pyrophosphate, sodium phosphate, potassium phosphate, sodium diphosphate, potassium diphosphate and the like. The amount of a sodium or potassium salt of a weakly ionized acid added to the reactants can range from about 50 to about 3500 parts per million, preferably about 100 to about 3000 parts per million, and more preferably about 100 to about 1500 parts per million of the initial reaction mixture. In the case of other basic materials, the amount should be equivalent to the amount stated for sodium and potassium salts of weakly ionized acids with regard to their ability to neutralize hydrogen ions in the system at hand. If a metal hydroxide such as sodium hydroxide or potassium hydroxide is utilized as the basic material, the amount added is no greater than would be required to neutralize the acids being formed in the reaction. For example, the use of sodium hydroxide in an amount of from about 25 to about 60 parts per million of the total reaction product resulted in production of satisfactory amounts of ethylene glycol and reduced amounts of methylal compared to the reaction containing no basic materials. In addition to those described previously, basic materials which can be used include zinc oxide, basic alumina, various basic thorium compounds and in general any basic material which will reduce the hydrogen ions of the acids produced without interfering with the reaction.

For purposes of this invention, amounts of at least 0.25 weight percent and as high as 25 weight percent of an organic peroxide, based on the weight of the reaction mixture, can be used in producing ethylene glycol from methanol, formaldehyde, organic peroxide and water, although, in general, reaction feeds employed in practicing the present invention will contain no higher than about 6 weight percent, e.g. from about 0.25 to about 6 weight percent, and preferably no higher than about 3 weight percent, e.g. about 0.75 to 3 weight percent, of organic peroxide. In most cases, the feed will also contain from about 45 to about 97 weight percent, preferably from about 80 to about 85 weight percent, of methanol, from about 0.5 to about 13 weight percent, preferably from about 2 to about 12 weight percent, of formaldehyde, and from about 0.5 to about 35 weight percent, preferably from about 2 to about 10 weight percent, of water.

This reaction will generally be carried out at a temperature of from about 100° C. to about 200° C., preferably from about 125° C. to about 175° C., at a residence time of no higher than about 8 hours, usually from about 0.25 hour to about 8 hours, and preferably from about 0.5 to about 4 hours. Generally, the higher the temperature, the lower the reaction time necessary to bring the reaction to a desired state of completion. There is little or no criticality in the pressure at which the reaction is carried out. Pressures of between autogenous pressure to about 600 psig can be utilized.

For the reaction of methanol with an organic peroxide in the absence of water and formaldehyde, the amount of methanol in the reaction feed will be from about 70 to about 95 weight percent, preferably from about 75 to about 90 weight percent. Correspondingly, the amount of organic peroxide in the reactant feed will be from about 5 to about 35 weight percent, and preferably from about 10 to about 25 weight percent. This reaction can be conducted at temperatures ranging from about 100° C. to about 200° C., preferably from about 155° C. to about 180° C. The time of reaction should not exceed about 8 hours, and preferably will be from about 0.5 to about 4 hours. Yields of ethylene glcyol can range from about 2 to about 8 weight percent of the total reaction products.

The organic peroxide employed in the process of this invention has the formula

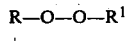

wherein R and R[1] are each an alkyl or aralkyl group having 3 to 12 carbon atoms. Organic peroxides which may be employed are, for example, di-tertiary-butyl peroxide, di-cumyl peroxide, tertiary-butyl cumyl peroxide and tertiary-butyl ethylbenzyl peroxide. The preferred organic peroxide is di-tertiary-butyl peroxide.

The reactions may be carried out batchwise, wherein a reactor such as a stirred autoclave is charged with the initial reaction mixture which is then subjected to reaction conditions, after which the entire reaction mixture is withdrawn and purified, semi-continuously, in which the initial reaction mixture is charged and product mixture withdrawn intermittently from the reactor, or continuously, wherein the reaction mixture is charged continuously and product mixture withdrawn continuously from the reactor. The product mixture may then be purified using conventional techniques, such as distillation or solvent extraction, to obtain ethylene glycol in the desired purity, preferably fiber grade, and by-products such as tertiary-butyl alcohol, methyl formate, glycerine, acetone, and any methylal which is formed during the process despite the addition of basic material in accordance with the invention.

The following examples will illustrate the invention:

EXAMPLES 1-21

Charges of the various feed compositions comprising methanol (MeOH), di-tertiary-butyl peroxide (DtBP), formaldehyde ($CH_2O$) as a mixture of 36 weight percent $CH_2O$ containing about 14 weight percent MeOH and 50 percent water ($H_2O$), sodium bicarbonate ($NaHCO_3$), except for Examples 13 and 14, in which no basic material was added, and any additional water in the charge not present in the charged formaldehyde solution, were prepared and charged to a 304 S.S. Hoke reactor at atmospheric pressure. The reactor was capped and placed in a thermostated oil bath held at the stated reaction temperature and allowed to react for the stated reaction temperature and the stated reaction time at autogenous pressure. After the reaction time was completed, the reactor was cooled by quenching, vented, discharged and analyzed by gas chromatography for contained ethylene glycol (EG) and methylal.

The results of these examples are shown in Table I which sets out the composition of the initial charge, the temperature and reaction time employed for the reaction and the amount of ethylene glycol produced in each example, both in terms of weight percent of the product mixture and in terms of moles of each product per mole of di-tertiary butyl peroxide consumed in the reaction.

TABLE I

| Example | Initial Charge, wt. % | | | | | Process Conditions | | Product | | Wt % methylal |
|---|---|---|---|---|---|---|---|---|---|---|
| | MeOH | DtBP | $CH_2O$ | $H_2O$ | $NaHCO_3$ | Temp, °C. | Reaction time, hrs | EG, wt % | moles EG / mole DtBP | |
| 1 | 84.07 | 1.23 | 6.14 | 8.53 | .026 | 155 | 1 | 5.18 | 9.9 | 1.42 |
| 2 | 81.77 | 1.19 | 7.12 | 9.89 | .025 | 155 | 1 | 5.29 | 10.5 | 2.36 |
| 3 | 82.35 | 2.98 | 6.13 | 8.51 | .026 | 155 | 1 | 6.26 | 4.9 | 1.46 |
| 4 | 80.07 | 2.89 | 7.12 | 9.89 | .025 | 155 | 1 | 6.72 | 5.5 | 2.29 |
| 5 | 79.36 | 5.97 | 6.13 | 8.51 | .026 | 155 | 1 | 7.70 | 3.0 | 1.07 |
| 6 | 77.16 | 5.78 | 7.13 | 9.90 | .025 | 155 | 1 | 7.71 | 3.1 | 2.02 |
| 7 | 84.02 | 1.23 | 6.17 | 8.57 | .013 | 155 | 1 | 4.89 | 9.4 | 2.28 |
| 8 | 81.59 | 1.20 | 7.2 | 10.0 | .013 | 155 | 1 | 5.00 | 9.8 | 3.50 |
| 9 | 92.04 | 1.38 | 2.75 | 3.82 | .015 | 155 | 1 | 3.12 | 5.3 | 0.19 |
| 10 | 89.41 | 1.33 | 3.87 | 5.38 | .014 | 155 | 1 | 3.93 | 7.0 | 0.44 |
| 11 | 92.0 | 3.49 | 1.88 | 2.61 | .015 | 155 | 1 | 3.41 | 2.3 | trace |
| 12 | 89.99 | 3.43 | 2.75 | 3.82 | .015 | 155 | 1 | 4.43 | 3.0 | 0.27 |
| 13 | 84.6 | 2.5 | 5.4 | 7.5 | —* | 155 | 1 | 5.51 | 5.2 | 4.01 |
| 14 | 80.85 | 1.25 | 5.4 | 12.5 | —* | 155 | 1 | 4.1 | 7.7 | 5.76 |
| 15 | 80.82 | 1.25 | 5.4 | 12.5 | .025 | 155 | 1 | 4.25 | 8.0 | 1.16 |
| 16 | 81.73 | 6.24 | 5.03 | 6.99 | .014 | 135 | 1 | 3.63 | —[1] | 0.54 |
| 17 | 81.73 | 6.24 | 5.03 | 6.99 | .014 | 135 | 2 | 5.40 | —[1] | 0.86 |
| 18 | 81.73 | 6.24 | 5.03 | 6.99 | .014 | 135 | 3 | 6.34 | —[1] | 1.04 |
| 19 | 81.73 | 6.24 | 5.03 | 6.99 | .014 | 135 | 4 | 6.80 | —[1] | 1.11 |
| 20 | 81.73 | 6.24 | 5.03 | 6.99 | .014 | 125 | 2 | 3.69 | —[1] | 0.54 |
| 21 | 81.73 | 6.24 | 5.03 | 6.99 | .014 | 125 | 4 | 5.39 | —[1] | 1.02 |

*Possible trace of $NaHCO_3$
[1]Examples 16 to 21 were partial conversion runs in which the extent of DtBP conversions were not analytically determined. However, stability of DtBP is such that any uncovered DtBP could be recycled.

As can be seen from the data in Table I, smaller amounts of methylal are produced in the process when sodium bicarbonate is added to the reactants compared to Examples 13 and 14 wherein no sodium bicarbonate was added.

In the control Examples 13 and 14, a trace of sodium bicarbonate may be present in the reaction due to the fact that the monomeric aqueous formaldehyde for the reactions was produced from paraformaldehyde. Thus, a small amount of hydrogen chloride was added to depolymerize the paraformaldehyde to aqueous monomeric formaldehyde. After the aqueous monomer was formed, a small amount of sodium bicarbonate was used to neutralize the solution using the color change of litmus paper to indicate neutralization. This might have resulted in the presence of a trace of sodium bicarbonate in Examples 13 and 14 wherein no additional sodium bicarbonate was added thus reducing slightly the amount of methylal produced in these examples. Although the traces of sodium bicarbonate which may have been present in Examples 13 and 14 would have been much lower than the 0.013 weight percent added in Examples 7 and 8, the fact that they could have resulted in some reduction in methylal production may have contributed to a narrowing of the differences between the methylal produced in Examples 13 and 14 wherein no bicarbonate was added and that produced in the remaining examples wherein bicarbonate in varying amounts was added, such as Example 8. Irrespective of this factor, however, the result of Example 8 as well as the other examples wherein bicarbonate was added illustrates that lower amounts of methylal are produced when higher amounts of sodium bicarbonate are utilized compared to control Examples 13 and 14.

material, a significantly larger amount of the by-product methylal was produced than in the other experiments.

TABLE II

| Example | Charge (wt %) | | | | Basic Materials | Run Length (Hrs.) | Products (wt %) | | moles EG / DtBP | Run T °C. |
|---|---|---|---|---|---|---|---|---|---|---|
| | H₂O | DtBP | CH₂O | MeOH | | | EG | MeAl | | |
| 22 | 5.0 | 6.0 | 8.0 | 81.0 | 0 | 2.0 | 7.6 | 2.94 | 3.0 | 155 |
| | | | | | NaHCO₃ | | | | | |
| 23 | 5.0 | 6.0 | 8.0 | 81.0 | 0.010 | 2.0 | 8.5 | 1.55 | 3.4 | 155 |
| 24 | 5.0 | 6.0 | 8.0 | 81.0 | 0.015 | 1.0 | 8.5 | 0.95 | 3.4 | 155 |
| 25 | 5.0 | 6.0 | 8.0 | 81.0 | 0.020 | 2.0 | 8.4 | 1.39 | 3.3 | 155 |
| 26 | 5.0 | 6.0 | 8.0 | 81.0 | 0.030 | 2.0 | 8.3 | 1.39 | 3.3 | 155 |
| 27 | 5.0 | 6.0 | 8.0 | 81.0 | 0.040 | 2.0 | 8.2 | 1.11 | 3.2 | 155 |
| 28 | 5.0 | 6.0 | 8.0 | 81.0 | 0.050 | 2.0 | 8.4 | 1.00 | 3.3 | 155 |
| | | | | | NaOAc | | | | | |
| 29 | 5.0 | 6.0 | 8.0 | 81.0 | 0.015 | 2.0 | 8.5 | 1.20 | 3.3 | 155 |
| 30 | 5.0 | 6.0 | 8.0 | 81.0 | 0.030 | 2.0 | 8.4 | 0.84 | 3.3 | 155 |
| 31 | 5.0 | 6.0 | 8.0 | 81.0 | 0.060 | 2.0 | 8.5 | 0.70 | 3.4 | 155 |
| 32 | 5.0 | 6.0 | 8.0 | 81.0 | 0.120 | 2.0 | 7.6 | 0.61 | 3.0 | 155 |
| 33 | 5.0 | 6.0 | 8.0 | 81.0 | 0.150 | 2.0 | 7.5 | 0.21 | 2.9 | 155 |
| | | | | | NaFo | | | | | |
| 34 | 5.0 | 6.0 | 8.0 | 81.0 | 0.015 | 1.0 | 8.0 | 0.85 | 3.3 | 155 |
| 35 | 5.0 | 6.0 | 8.0 | 81.0 | 0.030 | 1.0 | 8.0 | 0.61 | 3.3 | 155 |
| 36 | 5.0 | 6.0 | 8.0 | 81.0 | 0.045 | 1.0 | 8.4 | 0.55 | 3.4 | 155 |
| 37 | 5.0 | 6.0 | 8.0 | 81.0 | 0.060 | 1.0 | 8.1 | 0.47 | 3.3 | 155 |

EXAMPLES 22-37

An initial reaction mixture containing methanol (MeOH), di-tertiary-butyl peroxide (DtBP), formaldehyde (CH₂O) and water (H₂O) and as the basic material, sodium bicarbonate (NaHCO₃), sodium acetate (NaOAc) or sodium formate (NaFo) (except Example 22, in which no basic material was used), was charged to a stainless steel bomb which was sealed and heated under autogenous pressure. The formaldehyde used was contained in a mixture of about 55 weight percent of formaldehyde, about 35 weight percent of methanol, about 10 weight percent water and 25 parts per million sodium hydroxide. To obtain the 5 weight percent water content of the reactants, the formaldehyde mixture was diluted with methanol or water, whichever was needed, to achieve the desired proportions. After the prescribed reaction time, the product mixture was removed from the bomb and analyzed for ethylene glycol (EG) and other products such as methylal (MeAl).

The results of these examples are shown in Table II which sets out the composition of the initial charge, the temperature, reaction time employed for the reaction, the amount of ethylene glycol produced in each example, both in terms of weight percent of the product mixture and in terms of product EG per mole of di-tertiary-butyl peroxide consumed in the reaction. Methylal by-product produced is shown in weight percent of the product mixture. It should be noted that in Example 22, the only example in this table not including a basic

EXAMPLES 38-55

An initial reaction mixture containing methanol (MeOH), di-tertiary-butyl peroxide (DtBP), formaldehyde (CH₂O), water, and in some cases (Examples 41-55) sodium bicarbonate (NaHCO₃) was charged to a stainless steel bomb which was sealed and heated under autogenous pressure. The formaldehyde used in these examples contained a mixture of about 55 weight percent of formaldehyde, about 35 weight of methanol and about 10 weight percent water. As distinct from the formaldehyde used in Examples 22-37, no sodium hydroxide was present in this formaldehyde mixture. To obtain the 5 weight percent water content of the reactants, the formaldehyde mixture was diluted with methanol or water whichever was needed to achieve the proper proportions. After the prescribed reaction time, the product mixture was removed from the bomb and analyzed for ethylene glycol (EG) and methylal (MeAl).

The results of these examples are in Table III which sets out the composition of the initial charge, the temperature, reaction time employed for the reaction, and the amount of ethylene glycol produced in each example, both in terms of weight percent of the product mixture (under products wt %) and in terms of moles of ethylene glycol per mole of di-tertiary-butyl peroxide consumed in the reaction. Methylal by-product produced is shown in weight percent of the product mixture. It should be noted that as the sodium bicarbonate is increased from 50 to 1500 parts per million in the reactants, less by-product methylal is produced.

TABLE III

| Example | Charge (wt %) | | | | Parts Per Million NaHCO₃ | Run Length (Hrs.) | Products (wt %) | | moles EG / DtBP | Run T °C. |
|---|---|---|---|---|---|---|---|---|---|---|
| | H₂O | DtBP | CH₂O | MeOH | | | EG | MeAl | | |
| 38 | 5 | 6.0 | 8.0 | 81 | 0 | 1.0 | 6.141 | 6.517 | 2.45 | 155 |
| 39 | 5 | 6.0 | 8.0 | 81 | 0 | 1.0 | 6.445 | 6.312 | 2.58 | 155 |
| 40 | 5 | 6.0 | 8.0 | 81 | 0 | 1.0 | 6.853 | 5.34 | 2.73 | 155 |
| 41 | 5 | 6.0 | 8.0 | 81 | 50 | 1.0 | 7.403 | 2.190 | 2.94 | 155 |
| 42 | 5 | 6.0 | 8.0 | 81 | 50 | 1.0 | 8.193 | 2.037 | 3.26 | 155 |
| 43 | 5 | 6.0 | 8.0 | 81 | 50 | 1.0 | 7.729 | 2.134 | 3.07 | 155 |
| 44 | 5 | 6.0 | 8.0 | 81 | 250 | 1.0 | 7.655 | 1.092 | 3.04 | 155 |
| 45 | 5 | 6.0 | 8.0 | 81 | 250 | 1.0 | 7.957 | 1.044 | 3.16 | 155 |
| 46 | 5 | 6.0 | 8.0 | 81 | 250 | 1.0 | 7.797 | 1.053 | 3.10 | 155 |

TABLE III-continued

| Example | H$_2$O | Charge (wt %) DtBP | CH$_2$O | MeOH | Parts Per Million NaHCO$_3$ | Run Length (Hrs.) | Products (wt %) EG | MeAl | moles EG / DtBP | Run T °C. |
|---|---|---|---|---|---|---|---|---|---|---|
| 47 | 5 | 6.0 | 8.0 | 81 | 500 | 1.0 | 7.564 | .795 | 3.00 | 155 |
| 48 | 5 | 6.0 | 8.0 | 81 | 500 | 1.0 | 8.177 | .877 | 3.26 | 155 |
| 49 | 5 | 6.0 | 8.0 | 81 | 500 | 1.0 | 7.229 | .761 | 2.89 | 155 |
| 50 | 5 | 6.0 | 8.0 | 81 | 1000 | 1.0 | 7.394 | .542 | 2.95 | 155 |
| 51 | 5 | 6.0 | 8.0 | 81 | 1000 | 1.0 | 7.137 | .511 | 2.84 | 155 |
| 52 | 5 | 6.0 | 8.0 | 81 | 1000 | 1.0 | 6.235 | .512 | 2.48 | 155 |
| 53 | 5 | 6.0 | 8.0 | 81 | 1500 | 1.0 | 7.287 | .382 | 2.90 | 155 |
| 54 | 5 | 6.0 | 8.0 | 81 | 1500 | 1.0 | 6.449 | .455 | 2.56 | 155 |
| 55 | 5 | 6.0 | 8.0 | 81 | 1500 | 1.0 | 7.016 | .362 | 2.78 | 155 |

EXAMPLES 56-70

An initial reaction mixture containing methanol (MeOH), di-tertiary-butyl peroxide (DtBP), formaldehyde (CH$_2$O), water and with or without any of various buffers was charged to a stainless steel (316-SS) autoclave (300 cc). All the examples were carried out at 155° C. for 2 hours under autogenous pressures. All charges were stirred during the reaction except Examples 58 and 59. After the prescribed reaction time, the product mixture was removed from the bomb and analyzed for ethylene glycol (EG), formaldehyde (CH$_2$O) and methylal (MeAl). The various basic materials used are identified as follows: NaOH (sodium hydroxide), NaFo (sodium formate), HFo (formic acid), H$_3$PO$_4$ (phosphoric acid), Na$_4$P$_2$O$_7$10H$_2$O (pyrophosphate) and NaHCO$_3$ (sodium bicarbonate). The combination of phosphoric acid and sodium hydroxide of Example 66 produces sodium phosphate. The combination of oxalic acid and sodium hydroxide in Example 69 produces sodium oxalate.

The results of these examples are in Table IV which sets out the composition of the initial charge, temperature, reaction time employed for the reaction, basic materials and amount of ethylene glycol produced in each example, both in terms of weight percent of the product mixture and moles of ethylene glycol per mole of di-tertiary-butyl peroxide consumed in the reaction. The other products shown in the reaction product mixture are formaldehyde and methylal. Table IV illustrates that with the use of various basic materials, the amount of ethylene glycols produced can be maintained at a satisfactory level with a small amount of methylal by-product being produced. Where no basic material was used larger amounts of methylal were produced. In regard to Examples 64 and 65 where 5000 parts per million of sodium formate were added, low yields of ethylene glycol were obtained with the production of small amounts of methylal. Sodium formate (Examples 61-63) used as the basic material at a level of 1000 parts per million resulted in a satisfactory amount of ethylene glycol and a small amount of methylal. Example 70 in which sodium bicarbonate in an amount of 150 parts per million was utilized yielded a satisfactory amount of ethylene glycol but the amount of methylal produced was slightly higher than other runs employing the same amount of sodium bicarbonate shown in Table III. This discrepancy is not understood and the result of the experiment is believed to be anomalous. Sodium pyrophosphate (Examples 67-68) and sodium oxalate (Example 69) used as the basic material also yielded satisfactory amounts of ethylene glycol and small amounts of methylal. The addition of 60 parts per million of sodium hydroxide (Examples 58-60) yielded satisfactory amounts of ethylene glycol and reduced amounts of methylal compared to those results which contained no sodium hydroxide or any other basic material. The results of the above examples indicate that satisfactory amounts of ethylene glycol can be produced from methanol and formaldehyde and the coproduction of methylal can be kept low when a basic material is used in accordance with this invention.

TABLE IV

EFFECT OF BASIC MATERIALS ON ETHYLENE GLYCOL YIELD

| Example | H$_2$O | Charge Wt % DtBP | CH$_2$O | MeOH | Basic Materials Kind | Wt % | Run Length (Hrs.) | Products Wt % EG | CH$_2$O | MeAl | Moles EG / DtBP | Run Temp. °C. |
|---|---|---|---|---|---|---|---|---|---|---|---|---|
| 56 | 10 | 6.0 | 10 | 74 | None | — | 2 | 5.5 | 0.90 | 8.4 | 2.14 | 155 |
| 57 | 10 | 6.0 | 10 | 74 | None | — | 2 | 5.77 | 0.83 | 8.25 | 2.23 | 155 |
| 58* | 10 | 6.0 | 10 | 74 | NaOH | 0.006 | 2 | 7.7 | 1.4 | 6.2 | 3.06 | 155 |
| 59* | 10 | 6.0 | 10 | 74 | NaOH | 0.006 | 2 | 7.6 | 1.1 | 5.8 | 2.98 | 155 |
| 60 | 5.0 | 6.0 | 8 | 81 | NaOH | 0.006 | 2 | 7.0 | 0.9 | 2.3 | 2.75 | 155 |
| 61 | 10 | 6.0 | 10 | 74 | NaFo | 0.10 | 2 | 6.7 | 2.85 | 1.13 | 2.63 | 155 |
| 62 | 10 | 6.0 | 10 | 74 | NaFo HFo | 0.10 0.02 | 2 | 7.2 | 2.77 | 0.81 | 2.84 | 155 |
| 63 | 10 | 6.0 | 10 | 74 | NaFo HFo | 0.10 0.10 | 2 | 6.2 | 2.71 | 1.33 | 2.36 | 155 |
| 64 | 10 | 6.0 | 10 | 73.5 | NaFo | 0.50 | 2 | 2.64 | 1.25 | 0.32 | 1.02 | 155 |
| 65 | 10 | 6.0 | 10 | 73.4 | NaFo HFo | 0.50 0.10 | 2 | 2.01 | 1.16 | 0.18 | 0.78 | 155 |
| 66 | 10 | 6.0 | 10 | 74 | H$_3$PO$_4$ NaOH | 0.10 0.06 | 2 | 6.43 | 1.71 | 1.72 | 2.49 | 155 |
| 67 | 10 | 6.0 | 10 | 74 | Na$_4$P$_2$O$_7$.10H$_2$O H$_3$PO$_4$ | 0.30 0.04 | 2 | 7.30 | 1.87 | 1.14 | 2.82 | 155 |
| 68 | 10 | 6.0 | 10 | 74 | Na$_4$P$_2$O$_7$.10H$_2$O H$_3$PO$_4$ | 0.30 0.04 | 2 | 7.55 | 1.90 | 1.13 | 2.93 | 155 |
| 69 | 10 | 6.0 | 10 | 74 | Oxalic Acid NaOH | 0.10 0.09 | 2 | 6.43 | 2.59 | 1.42 | 2.50 | 155 |

TABLE IV-continued
EFFECT OF BASIC MATERIALS ON ETHYLENE GLYCOL YIELD

| Example | H$_2$O | Charge Wt % DtBP | CH$_2$O | MeOH | Basic Materials Kind | Wt % | Run Length (Hrs.) | Products Wt % EG | CH$_2$O | MeAl | Moles EG / DtBP | Run Temp. °C. |
|---|---|---|---|---|---|---|---|---|---|---|---|---|
| 70 | 10 | 6.0 | 10 | 74 | NaHCO$_3$ | 0.015 | 2 | 7.35 | 2.69 | 3.77 | 2.0 | 155 |

*Reaction Not Stirred

EXAMPLES 71–79

An initial reaction mixture containing methanol (MeOH), di-tertiary-butyl peroxide (DtBP), formaldehyde (CH$_2$O), water and with or without any of various basic materials was charged to a stainless steel (316-SS) autoclave (300 cc). The reaction was carried out at a temperature ranging from 154°–156° C. for a reaction time ranging from 0.75 hour to 2 hours under autogenous pressure. All runs were stirred. After the prescribed reaction time, the product mixture was removed from the autoclave and analyzed for ethylene glycol (EG) and methylal (MeAl). The materials used as basic materials are identified as NaOH (sodium hydroxide) and NaHCO$_3$ (sodium bicarbonate).

In Examples 71–74 where no basic materials were present, large amounts of methylal are produced. In Examples 75–76 where small amounts of sodium hydroxide were used, the amounts of methylal produced were significantly lower than in Examples 71–74 but higher than in Examples 77–79 in which sodium bicarbonate was used. Although Example 79 using 0.42 weight percent (4200 parts per million) sodium bicarbonate reduced the methylal content, a very small amount of ethylene glycol was produced. There are indications that in this run much of the formaldehyde was converted to formose sugars in view of the amber color, characteristic odor and very low formaldehyde accountability.

The results of these examples are in Table V which sets out the composition of the initial charge, the temperature, reaction time employed for the reaction, and the amount of ethylene glycol and methylal produced in each example.

TABLE V
EFFECT OF BASIC MATERIAL ON ETHYLENE GLYCOL AND METHYLAL PRODUCTION

| Examples | Reaction Charge Wt % H$_2$O | DtBP | CH$_2$O | MeOH | Basic Material Kind | Wt % | Run Length (Hrs.) | Run Temp. °C. | Products Wt % EG | MeAl |
|---|---|---|---|---|---|---|---|---|---|---|
| 71 | 2.3 | 1.5 | 11.2 | 85 | None | — | 2 | 156 | 4.6 | 15.2 |
| 72 | 2.3 | 1.5 | 11.2 | 85 | None | — | 2 | 156 | 3.7 | 13.6 |
| 73 | 2.3 | 1.5 | 11.2 | 85 | None | — | 2 | 154 | 6.9 | 15.3 |
| 74 | 2.3 | 1.5 | 11.2 | 85 | None | — | 0.75 | 155 | 4.6 | 11.8 |
| 75 | 2.3 | 1.5 | 11.2 | 85 | NaOH | .006 | 0.75 | 155 | 3.7 | 3.6 |
| 76 | 2.3 | 1.5 | 11.2 | 85 | NaOH | .006 | 0.75 | 155 | 4.5 | 4.3 |
| 77 | 2.3 | 1.5 | 11.2 | 85 | NaHCO$_3$ | 0.05 | 2 | 155 | 4.5 | 3.0 |
| 78 | 2.3 | 1.5 | 11.2 | 85 | NaHCO$_3$ | 0.10 | 2 | 155 | 4.4 | 1.5 |
| 79 | 2.3 | 1.5 | 11.2 | 85 | NaHCO$_3$ | 0.42 | 2 | 154 | 0.59 | 0.25 |

EXAMPLES 80–93

These examples illustrate the use of additional basic materials to reduce methylal production in the ethylene glycol process. An initial reaction mixture containing methanol (MeOH), di-tertiary-butyl peroxide (DtBP), formaldehyde (CH$_2$O), water (H$_2$O) and the basic material was charged to a glass reactor which in this case was a capped serum vial. The vial was placed in a pipe reactor filled with methanol and sealed. It was then placed in a thermostated oil bath held at 155° C. and allowed to react for 2 hours at autogenous pressure. After the prescribed reaction time, the product mixture was removed from the glass reactor and analyzed for ethylene glycol (EG) and methylal (MeAl).

The results of these examples are shown in Table VI which sets out the composition of the initial charge and the amounts of ethylene glycol and methylal produced. The basic materials used in the examples were zinc oxide (ZnO), bismuth oxide (Bi$_2$O$_3$), cerium oxide (Ce$_2$O), stannic oxide (SnO$_2$), thorium oxide (ThO$_2$), aluminum oxide (Al$_2$O$_3$) and sodium bicarbonate (NaHCO$_3$) for comparison purposes.

TABLE VI
EFFECT OF BASIC MATERIAL ON ETHYLENE GLYCOL AND METHYLAL PRODUCTION

| Examples | Reaction Charge Wt % MeOH | H$_2$O | DtBP | CH$_2$O | Basic Material Kind | Wt % | Products Wt % EG | Methylal |
|---|---|---|---|---|---|---|---|---|
| 80 | 87.25 | 0.75 | 2.0 | 10 | — | — | 7.52 | 4.92 |
| 81 | 87.25 | 0.75 | 2.0 | 10 | — | — | 6.80 | 4.39 |
| 82 | 87.25 | 0.75 | 2.0 | 10 | — | — | 6.35 | 3.68 |
| 83 | 87.25 | 0.75 | 2.0 | 10 | NaHCO$_3$ | 0.005 | 6.69 | 2.32 |
| 84 | 87.25 | 0.75 | 2.0 | 10 | ZnO | 0.4 | 6.43 | 0.90 |
| 85 | 87.25 | 0.75 | 2.0 | 10 | ZnO | 0.8 | 6.87 | 0.95 |
| 86 | 92.55 | 0.45 | 1.0 | 6.0 | — | — | 4.75 | 2.67 |
| 87 | 92.55 | 0.45 | 1.0 | 6.0 | — | — | 4.56 | 2.57 |
| 88 | 92.55 | 0.45 | 1.0 | 6.0 | ZnO | 2.0 | 4.44 | 0.40 |
| 89 | 92.55 | 0.45 | 1.0 | 6.0 | BiO$_2$ | 2.0 | 3.29 | 1.68 |

TABLE VI-continued
EFFECT OF BASIC MATERIAL ON ETHYLENE GLYCOL AND METHYLAL PRODUCTION

| | Reaction Charge Wt % | | | | Basic Material | | Products Wt % | |
|---|---|---|---|---|---|---|---|---|
| Examples | MeOH | H$_2$O | DtBP | CH$_2$O | Kind | Wt % | EG | Methylal |
| 90 | 92.55 | 0.45 | 1.0 | 6.0 | Ce$_2$O | 2.0 | 4.22 | 2.03 |
| 91 | 92.55 | 0.45 | 1.0 | 6.0 | SnO$_2$ | 2.0 | 4.77 | 2.33 |
| 92 | 92.55 | 0.45 | 1.0 | 6.0 | ThO$_2$ | 2.0 | 3.00 | 0.33 |
| 93 | 92.55 | 0.45 | 1.0 | 6.0 | Al$_2$O$_3$ | 2.0 | 5.03 | 1.71 |

The results of Examples 80 to 85 which utilized a feed stream consisting of 87.25 weight percent of methanol, 2.0 weight percent of di-tertiary-butyl peroxide, 10.0 weight percent of formaldehyde and 0.75 weight percent of water illustrate the improvement in terms of lower methylal production obtained when using zinc oxide as the basic material. Thus, substantially lower amounts of methylal were obtained in Examples 84 and 85 utilizing zinc oxide, as compared with Examples 80 to 82 which employed no basic material. Examples 84 and 85 also produced lower amounts of methylal than Example 83 which utilized 0.005 weight percent of sodium bicarbonate.

Examples 88 through 93 demonstrate the use of metal oxides as the basic material utilizing a feed stream consisting of 92.55 weight percent of methanol, 1.0 weight percent of di-tertiary-butyl peroxide, 6.0 weight percent of formaldehyde and 0.45 weight percent of water. Thus, zinc oxide (Example 88), bismuth oxide (Example 89), thorium oxide (Example 92) and aluminum oxide (Example 93) at a two weight percent level, all produced lower amounts of methylal compared to the control Examples 86 and 87 which utilized no basic material. The use of bismuth oxide (Example 89) and cerium oxide (Example 90) produced somewhat lower amounts of methylal than control Examples 86 and 87 but not as low as were obtained with the other metal oxides as the basic material in this series of examples.

EXAMPLES 93–100

These examples illustrate the effective use of sodium bicarbonate as the basic material in the incremental addition of the reactants.

An initial reaction mixture containing methanol (MeOH), a di-tertiary-butyl peroxide (DtBP), formaldehyde (CH$_2$O), water and sodium bicarbonate (NaHCO$_3$) was charged to a 304 stainless steel Hoke reactor at atmospheric pressure. The reactor was capped and placed in a thermostated oil bath held at 155° C. and allowed to react for 1 hour at autogenous pressure. After the first hour of reaction, additional reactants, indicated as the second stage, were added and the reaction continued for an additional hour. Additional reactants were added in the same manner as the second stage addition to provide additional stages as indicated in Table VII wherein the total amounts of reactants are indicated in the various stages of addition. After the last addition of reactants and the completion of the reaction (assumed to be one hour after the addition of the last portion of reactants), the reactor was cooled by quenching, vented, discharged and the contents analyzed by gas chromatography for ethylene glycol (EG) and other products.

The results of these examples are shown in Table VII which sets out the composition of the reactants charged to the reactor containing methanol in the various stages. The amounts of the reactants used are reported as weight percent of the total reactants. The amounts of ethylene glycol and methylal where described are reported as weight percent of the total reaction products.

TABLE VII
INCREMENTAL ADDITION OF DI-TERTIARY-BUTYL PEROXIDE AND FORMALDEHYDE TO METHANOL TO PRODUCE ETHYLENE GLYCOL

| Example | | H$_2$O | CH$_2$O | DtBP | NaHCO$_3$ | Temp. °C. | Reaction Time Hrs. | Wt % Products EG | Methylal |
|---|---|---|---|---|---|---|---|---|---|
| 93 | 1st stage | 5.4 | 3.89 | 1.0 | .022 | 155 | 1 | 3.76 | — |
| | 2nd stage (total) | 8.2 | 5.89 | 1.95 | .066 | 155 | +1 = 2 | 7.3 | .97 |
| 94 | 1st stage | 5.4 | 3.89 | 1.5 | .022 | 155 | 1 | 4.27 | — |
| | 2nd stage (total) | 8.1 | 5.47 | 2.9 | .066 | 155 | +1 = 2 | 7.74 | .96 |
| 95 | 1st stage | 5.4 | 3.88 | 1.0 | 0 | 155 | 1 | — | — |
| | 2nd stage (total) | 8.2 | 5.88 | 1.15 | .0083 | 155 | +1 = 2 | — | — |
| | 3rd stage (total) | 10.9 | 6.93 | 2.85 | .0168 | 155 | +1 = 3 | — | — |
| | 4th stage (total) | 13.3 | 9.59 | 3.70 | .0248 | 155 | +1 = 4 | 9.08 | 5.02 |
| 96 | 1st stage | 5.4 | 3.88 | 1.0 | .0085 | 155 | 1 | — | — |
| | 2nd stage (total) | 8.2 | 5.88 | 1.95 | .012 | 155 | +1 = 2 | — | — |
| | 3rd stage (total) | 10.9 | 6.93 | 2.85 | .025 | 155 | +1 = 3 | — | — |
| | 4th stage (total) | 13.2 | 9.59 | 3.71 | .032 | 155 | +1 = 4 | 9.46 | 3.47 |
| 97 | 1st stage | 5.4 | 3.88 | 1.0 | 0 | 155 | 1 | 3.45 | — |
| | 2nd stage (total) | 8.2 | 5.86 | 1.95 | 0 | 155 | +1 = 2 | 5.31 | — |
| | 3rd stage (total) | 10.9 | 7.80 | 2.86 | 0 | 155 | +1 = 3 | 6.76 | 6.93 |
| 98 | 1st stage | 5.4 | 3.88 | 1.0 | .018 | 155 | 1 | 3.57 | — |
| | 2nd stage (total) | 8.2 | 5.86 | 1.95 | .037 | 155 | +1 = 2 | 6.04 | — |
| | 3rd stage (total) | 10.9 | 7.80 | 2.84 | .054 | 155 | +1 = 3 | 8.32 | 1.93 |
| 99 | 1st stage | 6.9 | 5.0 | 1.50 | .026 | 155 | 1 | 5.48 | — |
| | 2nd stage (total) | 10.75 | 7.74 | 2.80 | .052 | 155 | +1 = 2 | 8.38 | 1.97 |
| 100 | 1st stage | 6.9 | 5.0 | 1.99 | .026 | 155 | 1 | 5.63 | — |

TABLE VII-continued
INCREMENTAL ADDITION OF DI-TERTIARY-BUTYL PEROXIDE AND FORMALDEHYDE TO METHANOL TO PRODUCE ETHYLENE GLYCOL

| Example | H₂O | CH₂O | DtBP | NaHCO₃ | Temp. °C. | Reaction Time Hrs. | Wt % Products EG | Methylal |
|---|---|---|---|---|---|---|---|---|
| 2nd stage (total) | 10.6 | 7.76 | 3.72 | .051 | 155 | +1 = 2 | 8.59 | 1.80 |

What is claimed is:

1. In a process for producing ethylene glycol by reacting methanol and an organic peroxide, said peroxide having the formula R—O—O—R$_1$ wherein R and R$_1$ each is an alkyl or aralkyl group containing from 3 to 12 carbon atoms, the improvement comprising adding to the reactants a basic material in an amount sufficient to reduce the hydrogen ions that are being formed in the reaction without unduly reducing the ethylene glycol production due to by-product formation.

2. The process of claim 1 wherein said basic material is present in an amount sufficient to reduce significantly the amount of methylal produced compared to the result wherein no basic material is present and the amount of said basic material is below that wherein formose sugars are produced in substantial amounts as indicated by the amber color and characteristic odor of said formose sugar.

3. The process of claim 1 wherein the basic material is selected from the group consisting of metal hydroxides wherein the metal is selected from an alkaline earth metal and alkali metal; and salts of said metal hydroxides and a weakly ionized acid.

4. The process of claim 3 wherein the basic material is selected from the group consisting of sodium hydroxide, potassium hydroxide and sodium or potassium salt of a weakly ionized acid, the anion of said acid selected from the group consisting of acetate, formate, oxalate, carbonate, bicarbonate and phosphate.

5. The process of claim 4 wherein the basic material is selected from the group consisting of sodium acetate, potassium acetate, sodium bicarbonate, potassium bicarbonate, sodium formate, potassium formate, sodium oxalate, potassium oxalate, sodium phosphate, potassium phosphate, sodium pyrophosphate and potassium pyrophosphate, said basic material present in an amount ranging from about 50 to about 3500 parts per million based on the total reaction mixture.

6. The process of claim 5 wherein the amount of basic material ranges from about 100 to about 3000 parts per million based on the total reactions mixture and the organic peroxide is di-tertiary-butyl peroxide.

7. The process of claim 6 wherein the basic material ranges from about 100 to 1500 parts per million based on the total reaction mixture.

8. In a process for producing ethylene glycol by reacting methanol, an organic peroxide and formaldehyde in the presence of water, said organic peroxide having the formula R—O—O—R$_1$, wherein R and R$_1$ each is an alkyl or aralkyl group containing 3 to 12 carbon atoms, the improvement comprising adding to the reactants, a basic material in an amount sufficient to reduce the hydrogen ions that are being formed in the reaction without unduly reducing the ethylene glycol production due to by-product formation.

9. The process of claim 8 wherein said basic material is present in an amount sufficient to reduce significantly the amount of methylal produced compared to the result wherein no basic material is present and the amount of said basic material is below that wherein formose sugars are produced in substantial amounts as indicated by the amber color and characteristic odor of said formose sugar.

10. The process of claim 8 wherein said basic material is zinc oxide.

11. The process of claim 8 wherein the basic material is selected from the group consisting of alkali metal and alkaline earth metal hydroxides and salts of said metal hydroxides and weakly ionized acids.

12. The process of claim 11 wherein the basic material is selected from the group consisting of sodium acetate, potassium acetate, sodium bicarbonate, potassium bicarbonate, sodium formate, potassium formate, sodium oxalate, potassium oxalate, sodium pyrophosphate, potassium pyrophosphate, sodium phosphate and potassium phosphate and the amount of basic material present ranges from about 50 to about 3500 parts per million of the initial reaction mixture.

13. The process of claim 12 wherein the amount of basic material ranges from about 100 to about 3000 parts per million based on the total reaction mixture and the organic peroxide is di-tertiary-butyl peroxide.

14. The process of claim 13 wherein the amount of basic material ranges from about 100 to about 1500 parts per million based on the total reaction mixture.

15. The process of claim 8 wherein the initial reaction mixture contains from about 45 to 97 weight percent of methanol, from about 0.25 to about 6 weight percent of di-tertiary-butyl peroxide, from about 0.5 to about 13 weight percent of formaldehyde and from about 0.5 to about 35 weight percent of water, the weight percentages based on the total reaction mixture and the reaction being carried out at a temperature from about 100° C. to about 200° C. for a reaction time of from about 0.25 to about 8 hours.

16. The process of claim 15 wherein the basic material is sodium bicarbonate present in an amount ranging from about 100 to about 1500 parts per million based on the total reaction mixture.

17. The process of claim 15 wherein the basic material is sodium acetate present in an amount ranging from about 100 to about 1500 parts per million based on the total reaction mixture.

18. The process of claim 15 wherein the basic material is sodium formate present in an amount ranging from about 100 to about 1500 parts per million based on the total reaction mixture.

19. The process of claim 15 wherein the basic material is sodium oxalate present in an amount ranging from about 100 to about 1500 parts per million based on the total reaction mixture.

20. The process of claim 15 wherein the basic material is sodium phosphate present in an amount ranging from about 100 to about 1500 parts per million based on the total reaction mixture.

21. The process of claim 15 wherein the basic material is sodium pyrophosphate present in an amount ranging from about 100 to about 3000 parts per million based on the total reaction mixture.

22. In a process for producing ethylene glycol by reacting methanol, di-tertiary-butyl peroxide, formaldehyde and water, the improvement comprising adding to the reactants, a basic material in an amount sufficient to reduce the hydrogen ions that are being formed in the reaction without unduly reducing the ethylene glycol production due to by-product formation in the presence of water from about 0.5 to about 35 weight percent based on the total reaction mixture.

23. The process of claim 22 wherein the water is present in amounts from about 2 to about 10 weight percent based on the total reaction mixture.

24. In a process for producing ethylene glycol by reacting methanol, di-tertiary-butyl peroxide, formaldehyde and water, the improvement comprising adding to the reactants, a basic material in an amount sufficient to reduce the hydrogen ions that are being formed in the reaction without unduly reducing the ethylene glycol production due to by-product formation in the presence of di-tertiary-butyl peroxide from about 0.25 to about 6 weight percent based on the total reaction mixture.

25. The process of claim 24 wherein the water is present in amounts ranging from about 2 to about 10 weight percent based on the total reaction mixture.

26. In a process for producing ethylene glycol by reacting methanol, di-tertiary-butyl peroxide, formaldehyde and water, the improvement comprising adding to the reactants, a basic material in an amount sufficient to reduce the hydrogen ions that are being formed in the reaction without unduly reducing the ethylene glycol production due to by-product formation in the presence of water from about 0.5 to about 35 weight percent based on the total reaction mixture and di-tertiary-butyl peroxide from about 0.25 to about 6 weight percent based on the total reaction mixture.

* * * * *